(12) United States Patent
Chinta

(10) Patent No.: US 8,686,208 B2
(45) Date of Patent: Apr. 1, 2014

(54) NITROGEN CONTAINING CATALYST FOR COUPLING REACTIONS

(75) Inventor: Sivadinarayana Chinta, Missouri City, TX (US)

(73) Assignee: Fina Technology, Inc., Houston, TX (US)

( * ) Notice: Subject to any disclaimer, the term of this patent is extended or adjusted under 35 U.S.C. 154(b) by 141 days.

(21) Appl. No.: 13/457,493

(22) Filed: Apr. 27, 2012

(65) Prior Publication Data

US 2012/0296135 A1    Nov. 22, 2012

Related U.S. Application Data

(60) Provisional application No. 61/488,770, filed on May 22, 2011.

(51) Int. Cl.
*C07C 1/207*    (2006.01)

(52) U.S. Cl.
USPC .......................................... 585/437; 585/469

(58) Field of Classification Search
USPC .................................................. 585/437, 469
See application file for complete search history.

(56) References Cited

U.S. PATENT DOCUMENTS

2011/0270006 A1    11/2011    Pelati et al.

OTHER PUBLICATIONS

Vishal Agarwal, et al.; "DFT Study of Nitrogen-Substituted FAU: Effects of Ion Exchange and Aluminum Content on Base Strength"; J. Phys. Chem. C 2011, 115 (1), pp. 188-194; DOI: 10.1021/jp106971u. Publication Date (Web) Dec. 9, 2010; pp. 188-189.

*Primary Examiner* — Thuan D Dang

(57) ABSTRACT

A process for making styrene including providing a $C_1$ source to a reactor containing a catalyst and reacting toluene with the $C_1$ source in the presence of the catalyst to form a product stream comprising ethylbenzene and styrene. The $C_1$ source can be selected from the group of methanol, formaldehyde, formalin, trioxane, methylformcel, paraformaldehyde, methylal, dimethyl ether, and combinations thereof, and wherein the catalyst contains a nitrogen-substituted zeolite.

1 Claim, 2 Drawing Sheets

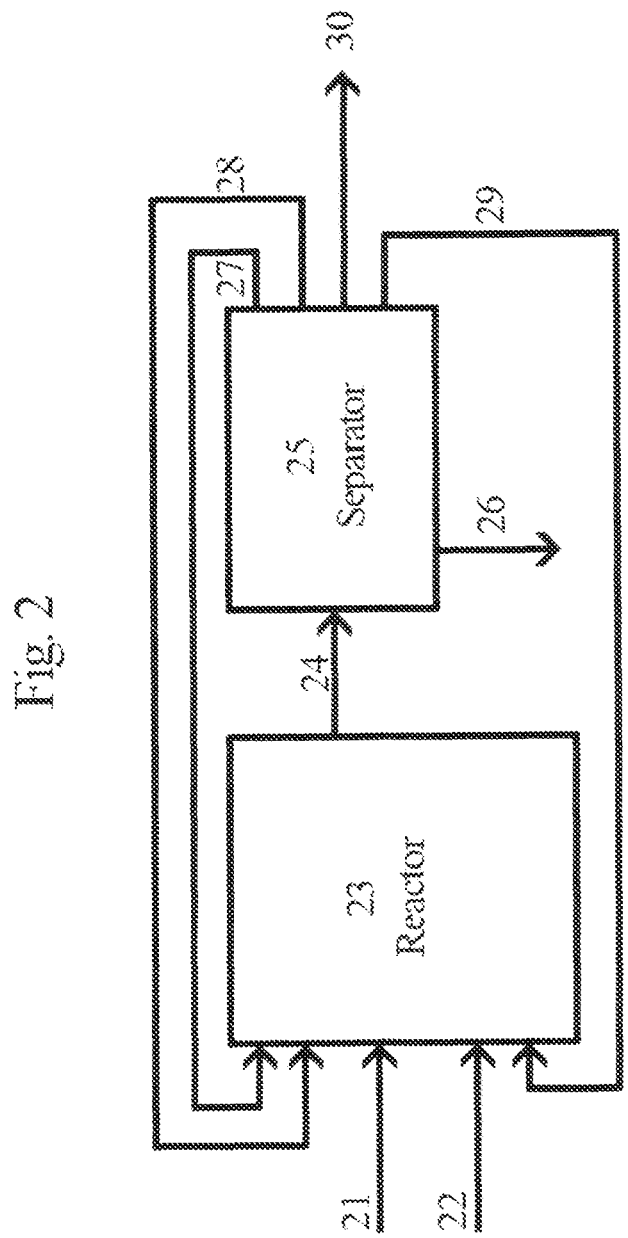

NITROGEN CONTAINING CATALYST FOR COUPLING REACTIONS

CROSS-REFERENCE TO RELATED APPLICATIONS

This application claims priority to U.S. Provisional Patent No. 61/488,770 filed on May 22, 2011.

FIELD

The present invention relates to coupling reactions. More specifically, the present invention relates to modified zeolite catalysts for use in coupling reactions.

BACKGROUND

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and reduced polyalkylated content. When both alkylation and transalkylation processes are used, two separate reactors, each with its own catalyst, can be employed for each of the processes.

Styrene is a monomer used in the manufacture of many plastics. Styrene is commonly produced by making ethylbenzene, which is then dehydrogenated to produce styrene. Ethylbenzene is typically formed by one or more aromatic conversion processes involving the alkylation of benzene.

Benzene can be obtained from the hydrodealkylation of toluene that involves heating a mixture of toluene with excess hydrogen to elevated temperatures (for example 500° C. to 600° C.) in the presence of a catalyst. Under these conditions, toluene can undergo dealkylation according to the chemical equation: $C_6H_5CH_3+H_2 \rightarrow C_6H_6+CH_4$ This reaction requires energy input and as can be seen from the above equation, produces methane as a byproduct, which is typically separated and may used as heating fuel for the process.

Another known process includes the alkylation of toluene to produce styrene and ethylbenzene. In this alkylation process, various aluminosilicate catalysts are utilized to react methanol and toluene to produce styrene and ethylbenzene. However, such processes have been characterized by having very low yields in addition to having very low selectivity to styrene and ethylbenzene.

It is desirable therefore to achieve a process having a high yield and selectivity to styrene and ethylbenzene. Even further, it is desirable to achieve a process having a high yield and selectivity to styrene such that the step of dehydrogenation of ethylbenzene to produce styrene can be avoided.

SUMMARY

The present invention in its many embodiments relates to a method of making styrene. In an embodiment, either by itself of in combination with other embodiments, the method of preparing a catalyst includes providing a substrate and a first solution including a nitrogen containing material, contacting the substrate with the nitrogen containing material and obtaining a catalyst including nitrogen. The contacting of the substrate with the nitrogen containing material can subject the substrate to the substitution of oxygen with nitrogen. The substrate can be a zeolite, optionally, the substrate is a zeolite selected from the group consisting of faujasites.

In an embodiment, either by itself of in combination with other embodiments, the nitrogen containing material can be selected from the group of ammonia, an alkyl amine, and any combinations thereof.

In an embodiment, either by itself of in combination with other embodiments, the method can further include contacting the catalyst including nitrogen with a second solution including a promoter, that can be one or more of Co, Mn, Ti, Zr, V, Nb, K, Cs, Ga, B, P, Rb, Ag, Na, Cu, Mg, Fe, Mo, Ce, and any combinations thereof. The catalyst can include the promoter in amounts ranging from 0.1 wt % to 5 wt % based on the total weight of the catalyst. Optionally, a promoter source is combined with the $C_1$ source prior to contact with the catalyst.

In an embodiment, the catalyst is capable of effecting a reaction of at least a portion of a $C_1$ source with toluene to form a product stream including one or more of styrene or ethylbenzene.

Another embodiment of the present invention includes a catalyst having a nitrogen-substituted zeolite support and a promoter. The promoter is supported onto the zeolite support by ion exchange. The ion exchange can be performed in an aqueous medium utilizing water soluble promoter precursors. Optionally, a nitrogen source is combined with a substrate material that is subsequently combined with the zeolite support including at least one promoter to form a supported catalyst including at least one promoter. In an embodiment, the catalyst is capable of effecting a reaction of at least a portion of a $C_1$ source with toluene to form a product stream including one or more of styrene or ethylbenzene, wherein the catalyst is capable of effecting selectivity to styrene of greater than 30 mol %.

In yet another embodiment of the present invention, a process for making styrene includes providing a $C_1$ source to a reactor including a catalyst and reacting toluene with the $C_1$ source in the presence of the catalyst to form a product stream including ethylbenzene and styrene. The $C_1$ source is selected from the group consisting of methanol, formaldehyde, formalin, trioxane, methylformcel, paraformaldehyde, methylal, and combinations thereof. The nitrogen-substituted zeolite is formed through contacting a zeolite with a nitrogen containing material the subjects the zeolite to the substitution of oxygen with nitrogen within the structure of the zeolite. The nitrogen containing material is selected from the group of ammonia, an alkyl amine, and any combinations thereof. The catalyst includes at least one promoter in amounts ranging from 0.1 wt % to 5 wt % based on the total weight of the catalyst, the promoter selected from the group of Co, Mn, Ti, Zr, V, Nb, K, Cs, Ga, B, P, Rb, Ag, Na, Cu, Mg, Fe, Mo, Ce, and any combinations thereof.

Other possible embodiments include two or more of the above embodiments of the invention. In an embodiment the method includes all of the above embodiments and the various procedures can be carried out in any order.

BRIEF DESCRIPTION OF THE DRAWINGS

FIG. 2 illustrates a flow chart for the production of styrene by the reaction of formaldehyde and toluene, wherein methanol and toluene are fed into a reactor, wherein the methanol is converted to formaldehyde and the formaldehyde is reacted with toluene to produce styrene.

DETAILED DESCRIPTION

Figure 1:
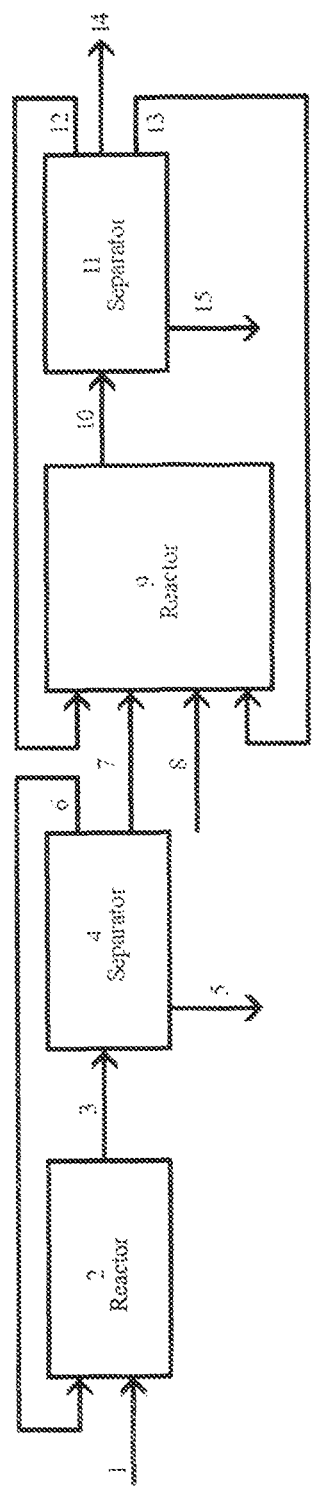
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene to produce styrene.

The present invention includes a catalyst for use in coupling reactions. More specifically, the present invention includes a zeolitic catalyst for use in alkylation reactions involving toluene with methanol and/or formaldehyde as reactants. The zeolitic catalyst of the present invention may contain a nitrogen-substituted zeolite having enhanced basicity and increased pore volume.

In an embodiment of the current invention, toluene is reacted with a carbon source capable of coupling with toluene to form ethylbenzene or styrene, which can be referred to as a $C_1$ source, to produce styrene and ethylbenzene. In an embodiment, the $C_1$ source includes methanol or formaldehyde or a mixture of the two. In an alternative embodiment, toluene is reacted with one or more of the following: formalin, trioxane, methylformcel, paraformaldehyde and methylal. In a further embodiment, the $C_1$ source is selected from the group of methanol, formaldehyde, formalin (37-50% $H_2CO$ in solution of water and MeOH), trioxane (1,3,5-trioxane), methylformcel (55% $H_2CO$ in methanol), paraformaldehyde, dimethyl ether, and methylal (dimethoxymethane), and combinations thereof.

Formaldehyde can be produced either by the oxidation or dehydrogenation of methanol.

In an embodiment, formaldehyde is produced by the dehydrogenation of methanol to produce formaldehyde and hydrogen gas. This reaction step produces a dry formaldehyde stream that may be preferred, as it would not require the separation of the water prior to the reaction of the formaldehyde with toluene. The dehydrogenation process is described in the equation below:

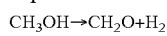

$$CH_3OH \rightarrow CH_2O + H_2$$

Formaldehyde can also be produced by the oxidation of methanol to produce formaldehyde and water. The oxidation of methanol is described in the equation below:

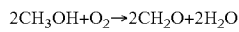

$$2CH_3OH + O_2 \rightarrow 2CH_2O + 2H_2O$$

In the case of using a separate process to obtain formaldehyde, a separation unit may then be used in order to separate the formaldehyde from the hydrogen gas or water from the formaldehyde and unreacted methanol prior to reacting the formaldehyde with toluene for the production of styrene. This separation would inhibit the hydrogenation of the formaldehyde back to methanol. Purified formaldehyde could then be sent to a styrene reactor and the unreacted methanol could be recycled.

Although the reaction has a 1:1 molar ratio of toluene and the $C_1$ source, the ratio of the feedstreams is not limited within the present invention and can vary depending on operating conditions and the efficiency of the reaction system. If excess toluene or $C_1$ source is fed to the reaction zone, the unreacted portion can be subsequently separated and recycled back into the process. In one embodiment the ratio of toluene:$C_1$ source can range from between 100:1 to 1:100. In alternate embodiments the ratio of toluene:$C_1$ source can range from 50:1 to 1:50; from 20:1 to 1:20; from 10:1 to 1:10; from 5:1 to 1:5; from 2:1 to 1:2. In a specific embodiment, the ratio of toluene:$C_1$ source can range from 2:1 to 5:1.

In FIG. 1 there is a simplified flow chart of one embodiment of the styrene production process described above. In this embodiment, a first reactor (2) is either a dehydrogenation reactor or an oxidation reactor. This reactor is designed to convert the first methanol feed (1) into formaldehyde. The gas product (3) of the reactor is then sent to a gas separation unit (4) where the formaldehyde is separated from any unreacted methanol and unwanted byproducts. Any unreacted methanol (6) can then be recycled back into the first reactor (2). The byproducts (5) are separated from the formaldehyde (7).

In one embodiment the first reactor (2) is a dehydrogenation reactor that produces formaldehyde and hydrogen and the separation unit (4) is a membrane capable of removing hydrogen from the product stream (3).

In an alternate embodiment the first reactor (2) is an oxidative reactor that produces product stream (3) comprising formaldehyde and water. The product stream (3) comprising formaldehyde and water can then be sent to the second reactor (9) without a separation unit (4).

The formaldehyde feed stream (7) is then reacted with a feed stream of toluene (8) in a second reactor (9). The toluene and formaldehyde react to produce styrene. The product (10) of the second reactor (9) may then be sent to an optional separation unit (11) where any unwanted byproducts (15) such as water can separated from the styrene, unreacted formaldehyde and unreacted toluene. Any unreacted formaldehyde (12) and the unreacted toluene (13) can be recycled back into the reactor (9). A styrene product stream (14) can be removed from the separation unit (11) and subjected to further treatment or processing if desired.

The operating conditions of the reactors and separators will be system specific and can vary depending on the feedstream composition and the composition of the product streams. The reactor (9) for the reaction of toluene and formaldehyde will operate at elevated temperatures and may contain a basic or neutral catalyst system. The temperature can range in a non-limiting example from 250° C. to 750° C., optionally from 300° C. to 500° C., optionally from 375° C. to 450° C. The pressure can range in a non-limiting example from 0.1 atm to 70 atm, optionally from 0.1 atm to 35 atm, optionally from 0.1 atm to 10 atm, optionally from 0.1 atm to 5 atm.

FIG. 2 is a simplified flow chart of another embodiment of the styrene process discussed above. A $C_1$ source containing feed stream (21) is fed along with a feed stream of toluene (22) in a reactor (23). Toluene and the $C_1$ source then react to produce styrene. The product (24) of the reactor (23) may then be sent to an optional separation unit (25) where any unwanted byproducts (26) can be separated from the styrene, and any unreacted $C_1$ source, unreacted methanol, unreacted formaldehyde and unreacted toluene. Any unreacted methanol (27), unreacted formaldehyde (28) and the unreacted toluene (29) can be recycled back into the reactor (23). A styrene product stream (30) can be removed from the separation unit (25) and subjected to further treatment or processing if desired.

The operating conditions of the reactors and separators will be system specific and can vary depending on the feedstream composition and the composition of the product streams. The reactor (23) for the reactions of methanol to formaldehyde and toluene with a $C_1$ source, such as formaldehyde, will operate at elevated temperatures and may contain a basic or neutral catalyst system. The temperature can range in a non-limiting example from 250° C. to 750° C., optionally from 300° C. to 500° C., optionally from 375° C. to 450° C. The pressure can range in a non-limiting example from 0.1 atm to 70 atm, optionally from 0.1 atm to 35 atm, optionally from 0.1 atm to 10 atm, optionally from 0.1 atm to 5 atm.

Improvement in side chain alkylation selectivity may be achieved by treating a molecular sieve zeolite catalyst with chemical compounds to inhibit the external acidic sites and minimize aromatic alkylation on the ring positions. Another means of improvement of side chain alkylation selectivity can be to impose restrictions on the catalyst structure to facilitate side chain alkylation. In one embodiment the catalyst used in an embodiment of the present invention is a basic or neutral catalyst. In another embodiment, the catalyst used in the present invention is treated with nitrogen in order to increase the basicity of the catalyst.

The acidity of zeolitic materials may present problems in catalytic performance, specifically in the alkylation of toluene with methanol and/or formaldehyde. The acidity, as well as the basicity, of the zeolitic material is dependent upon the amount of acid sites on the zeolitic material. The amount and/or density of acid sites can be reduced and thus the acidity of the zeolite can be reduced by substituting nitrogen for oxygen in the $SiO_4^-$ and/or $AlO_4^-$ of the zeolite, therefore, the amount of acidity/basicity is related to the degree of isomorphous substitution of nitrogen for oxygen in $SiO_4$ and/or $AlO_4$. The modification of the zeolite by substitution alters the basicity of the zeolite framework and changes the shape selectivity of the zeolite. Unlike grafting procedures, substitution does not significantly affect the pore diameter of the zeolite. Thus, substitution procedures for increase basicity can also have the added benefit of preserving pore volume for increased catalytic performance.

Prior to the addition of promoters, the oxygen present in the $SiO_4^-$ and $AlO_4^-$ of the zeolite may be replaced with nitrogen. Nitrogen-substituted zeolites, amorphous silicates, and aluminophosphates may be prepared by high-temperature treatment of the starting material with a nitrogen containing material. In an embodiment, the nitrogen containing material is selected from ammonia ($NH_3$) or an alkyl amine such as methyl amine and ethyl amine or any combinations thereof.

In an embodiment, the nitrogen containing material is contacted with a non-promoted zeolite under temperatures of at least 100° C. In another embodiment, the nitrogen containing material is contacted with a non-promoted zeolite under temperatures ranging from 200 to 1000° C. In a further embodiment, the nitrogen containing material is contacted with a non-promoted zeolite under temperatures ranging from 600 to 800° C. In one specific embodiment, the oxygen present in the zeolite may be replaced with nitrogen by contacting a non-promoted zeolite with ammonia at temperatures ranging from about 600 to about 800° C.

After the substitution of nitrogen for oxygen in the zeolite or other zeolite-like materials, the addition of promoters can be done in any suitable manner as is normally done with a zeolite or zeolite-like material.

In another non-limiting example the zeolite can be modified with alkali metal salts. In an embodiment, the zeolite can be modified with a nitrogen containing material. In an alternative embodiment, the zeolite can be modified with a promoter selected from the group of sodium hydroxide (NaOH), potassium hydroxide (KOH), magnesium hydroxide ($Mg(OH)_2$), and calcium carbonate ($CaCO_3$), and combinations thereof. In another embodiment, the zeolite can be promoted with alkali metal ions or basic salts via ion exchange, impregnation or the like. In a further embodiment, the promoter can exchange with an element within the zeolite or amorphous material and/or be attached to the zeolite or amorphous material in an occluded manner.

The catalytic reaction systems suitable for this invention can include one or more of the zeolite or amorphous materials modified for side chain alkylation selectivity. A non-limiting example can be a zeolite promoted with one or more of the following: Co, Mn, Ti, Zr, V, Nb, K, Cs, Ga, B, P, Rb, Ag, Na, Cu, Mg, Fe, Mo, Ce, or combinations thereof. In an embodiment, the zeolite can be promoted with one or more of Ce, Cu, P, Cs, B, Co, Ga, or combinations thereof. The promoter can exchange with an element within the zeolite or amorphous material and/or be attached to the zeolite or amorphous material in an occluded manner. In an embodiment the amount of promoter is determined by the amount needed to yield less than 0.5 mol % of ring alkylated products such as xylenes from a coupling reaction of toluene and a $C_1$ source.

In an embodiment, the catalyst contains greater than 0.1 wt % of at least one promoter based on the total weight of the catalyst. In another embodiment, the catalyst contains up to 5 wt % of at least one promoter. In an embodiment, the catalyst contains from 0.1 to 5 wt % of at least one promoter, optionally from 0.1 to 3 wt %, optionally from 0.1 to 1 wt %.

Zeolite materials suitable for this invention may include silicate-based zeolites and amorphous compounds such as faujasites, mordenites, etc. Silicate-based zeolites are made of alternating $SiO_4^-$ and $MO_x$ tetrahedra, where M is an element selected from the Groups 1 through 16 of the Periodic Table (new IUPAC). These types of zeolites have 4, 6, 8, 10, or 12-membered oxygen ring channels. An example of the zeolites of the present invention can include faujasites, such as an X-type or Y-type zeolite and zeolite beta. Zeolite-like materials can also be an effective substrate. Alternate molecular sieves also contemplated are zeolite-like materials such as the crystalline silicoaluminophosphates (SAPO) and the aluminophosphates (ALPO) and the like.

In an embodiment, the zeolite materials suitable for this invention are characterized by silica to alumina ratio (Si/Al) of less than 1.5. In another embodiment, the zeolite materials are characterized by a Si/Al ratio ranging from 1.0 to 200, optionally from 1.0 to 100, optionally from 1.0 to 50, optionally from 1.0 to 10, optionally from 1.0 to 2.0, optionally from 1.0 to 1.5.

The present catalyst is adaptable to use in the various physical forms in which catalysts are commonly used. The catalyst of the invention may be used as a particulate material in a contact bed or as a coating material on structures having a high surface area. If desired, the catalyst can be deposited with various catalyst binder and/or support materials.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" as used herein is not meant to indicate that this component is necessarily inactive, while the other metals and/or promoters are the active species. On the contrary, the substrate can be an active part of the catalyst. The term "substrate" would merely imply that the substrate makes up a significant quantity, generally 10% or more by weight, of the entire catalyst. The promoters individually can range from 0.01% to 60% by weight of the catalyst, optionally from 0.01% to 50%, optionally from 0.01% to 40%, optionally from 0.01% to 30%, optionally from 0.01% to 20%, optionally from 0.01% to 10%, optionally from 0.01% to 5%. If more than one promoter is combined, they together generally can range from 0.01% up to 70% by weight of the catalyst, optionally from 0.01% to 50%, optionally from 0.01% to 30%, optionally from 0.01% to 15%, optionally from 0.01% to 5%. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can include an alumina or aluminate framework as a support. Upon calcination these elements can be altered, such as through oxidation which would increase the relative content of oxygen within the final catalyst structure. The combination of the catalyst of the present invention combined with additional elements such as a binder, extrusion aid, structured material, or other additives, and their respective calcination products, are included within the scope of the invention.

The present invention is not limited by the method of catalyst preparation, and all suitable methods should be considered to fall within the scope herein. Particularly effective techniques are those utilized for the preparation of solid catalysts. Conventional methods include co-precipitation from an aqueous, an organic or a combination solution-dispersion, impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

The promoter elements can be added to or incorporated into the substrate in any appropriate form. In an embodiment, the promoter elements are added to the substrate by mechanical mixing, by impregnation in the form of solutions or suspensions in an appropriate liquid, or by ion exchange. In a more specific embodiment, the promoter elements are added to the substrate by impregnation in the form of solutions or suspensions in a liquid selected from the group of acetone, anhydrous (or dry) acetone, methanol, and aqueous solutions.

In another more specific embodiment, the promoter is added to the substrate by ion exchange. Ion exchange may be performed by conventional ion exchange methods in which sodium, hydrogen, or other inorganic cations that may be typically present in a substrate are at least partially replaced via a fluid solution. In an embodiment, the fluid solution can include any medium that will solubilize the cation without adversely affecting the substrate. In an embodiment, the ion exchange is performed by heating a solution containing any promoter selected from the group of Co, Mn, Ti, Zr, V, Nb, K, Cs, Ga, B, P, Rb, Ag, Na, Cu, Mg, Fe, Mo, Ce, and any combinations thereof in which the promoter(s) is(are) solubilized in the solution, which may be heated, and contacting the solution with the substrate. In another embodiment, the ion exchange includes heating a solution containing any one selected from the group of Ce, Cu, P, Cs, B, Co, Ga, and any combinations thereof. In another embodiment, the ion exchange includes heating a solution containing Cs. In an embodiment, the solution is heated to temperatures ranging from 50 to 120° C. In another embodiment, the solution is heated to temperatures ranging from 80 to 100° C.

The solution for use in the ion exchange method may include any fluid medium. A non-fluid ion exchange is also possible and within the scope of the present invention. In an embodiment, the solution for use in the ion exchange method includes an aqueous medium or an organic medium. In a more specific embodiment, the solution for use in the ion exchange method includes water.

The promoters may be incorporated into the substrate in any order or arrangement. In an embodiment, all of the promoters are simultaneously incorporated into the substrate. In more specific embodiment, each promoter is in an aqueous solution for ion-exchange with and/or impregnation to the substrate. In another embodiment, each promoter is in a separate aqueous solution, wherein each solution is simultaneously contacted with the substrate for ion-exchange with and/or impregnation to the substrate. In a further embodiment, each promoter is in a separate aqueous solution, wherein each solution is separately contacted with the substrate for ion-exchange with and/or impregnation to the substrate.

When slurries, precipitates or the like are prepared, they may be dried, usually at a temperature sufficient to volatilize the water or other carrier, such as from 100° C. to 250° C., with or without vacuum. Irrespective of how the components are combined and irrespective of the source of the components, the dried composition is generally calcined in the presence of an oxygen-containing gas, usually at temperatures between about 300° C. and about 900° C. for from 1 to 24 hours. The calcination can be in an oxygen-containing atmosphere, or alternately in a reducing or inert atmosphere.

The prepared catalyst can be ground, pressed, sieved, shaped and/or otherwise processed into a form suitable for loading into a reactor. The reactor can be any type known in the art to make catalyst particles, such as a fixed bed, fluidized bed, or swing bed reactor. Optionally an inert material can be used to support the catalyst bed and to place the catalyst within the bed. Depending on the catalyst, a pretreatment of the catalyst may, or may not, be necessary. For the pretreatment, the reactor can be heated to elevated temperatures, such as 200° C. to 900° C. with an air flow, such as 100 mL/min, and held at these conditions for a length of time, such as 1 to 3 hours. Then, the reactor can be brought to the operating temperature of the reactor, for example 300° C. to 550° C., or optionally down to any desired temperature, for instance down to ambient temperature to remain under a purge until it is ready to be put in service. The reactor can be kept under an inert purge, such as under a nitrogen or helium purge.

Embodiments of reactors that can be used with the present invention can include, by non-limiting examples: fixed bed reactors; fluid bed reactors; moving bed reactors; and entrained bed reactors. Reactors capable of the elevated temperature as described herein, and capable of enabling contact of the reactants with the catalyst, can be considered within the scope of the present invention. Embodiments of the particular reactor system may be determined based on the particular design conditions and throughput, as by one of ordinary skill in the art, and are not meant to be limiting on the scope of the present invention. An example of a suitable reactor can be a fluid bed reactor having catalyst regeneration capabilities. This type of reactor system employing a riser can be modified as needed, for example by insulating or heating the riser if thermal input is needed, or by jacketing the riser with cooling water if thermal dissipation is required. These designs can also be used to replace catalyst while the process is in operation, by withdrawing catalyst from the regeneration vessel from an exit line or adding new catalyst into the system while in operation.

In another embodiment, the one or more reactors may include one or more catalyst beds. In the event of multiple beds, an inert material layer can separate each bed. The inert material can comprise any type of inert substance. In an embodiment, a reactor includes between 1 and 25 catalyst beds. In a further embodiment, a reactor includes between 2 and 10 catalyst beds. In a further embodiment, a reactor includes between 2 and 5 catalyst beds. In addition, the $C_1$ source and toluene may be injected into a catalyst bed, an inert material layer, or both. In a further embodiment, at least a portion of the $C_1$ source is injected into a catalyst bed(s) and at least a portion of the toluene feed is injected into an inert material layer(s).

In an alternate embodiment, the entire $C_1$ source is injected into a catalyst bed(s) and all of the toluene feed is injected into an inert material layer(s). In another embodiment, at least a portion of the toluene feed is injected into a catalyst bed(s) and at least a portion the $C_1$ source is injected into an inert material layer(s). In a further embodiment, all of the toluene feed is injected into a catalyst bed(s) and the entire $C_1$ source is injected into an inert material layer(s).

The toluene and $C_1$ source coupling reaction may have a toluene conversion percent greater than 0.01 mol %. In an embodiment the toluene and $C_1$ source coupling reaction is capable of having a toluene conversion percent in the range of from 0.05 mol % to 40 mol %. In a further embodiment the toluene and $C_1$ source coupling reaction is capable of having a toluene conversion in the range of from 2 mol % to 40 mol %, optionally from 5 mol % to 35 mol %, optionally from 10 mol % to 30 mol %.

In an embodiment the toluene and $C_1$ source coupling reaction is capable of selectivity to styrene greater than 1 mol %. In another embodiment, the toluene and $C_1$ source coupling reaction is capable of selectivity to styrene in the range of from 1 mol % to 99 mol %. In an embodiment the toluene to a $C_1$ source coupling reaction is capable of selectivity to ethylbenzene greater than 1 mol %. In another embodiment, the toluene and $C_1$ source coupling reaction is capable of selectivity to ethylbenzene in the range of from 1 mol % to 99 mol %. In an embodiment the toluene and $C_1$ source coupling reaction is capable of yielding less than 0.5 mol % of ring alkylated products such as xylenes.

As used herein, the term "conversion" refers to the percentage of reactant (e.g. toluene) that undergoes a chemical reaction.

$$X_{Tol} = \text{conversion of toluene (mol \%)} = (\text{Tol}_{in} - \text{Tol}_{out})/\text{Tol}_{in}$$

$$X_{MeOH} = \text{conversion of methanol to styrene+ethylbenzene (mol \%)}$$

As used herein, the term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "selectivity" refers to the relative activity of a catalyst in reference to a particular compound in a mixture. Selectivity is quantified as the proportion of a particular product relative to all other products.

$$S_{Sty} = \text{selectivity of toluene to styrene (mol \%)} = \text{Sty}_{out}/\text{Tol}_{converted}$$

$$S_{Bz} = \text{selectivity of toluene to benzene (mol \%)} = \text{Benzene}_{out}/\text{Tol}_{converted}$$

$$S_{EB} = \text{selectivity of toluene to ethylbenzene (mol \%)} = \text{EB}_{out}/\text{Tol}_{converted}$$

$$S_{Xyl} = \text{selectivity of toluene to xylenes (mol \%)} = \text{Xylenes}_{out}/\text{Tol}_{converted}$$

$$S_{Sty+EB}(\text{MEOH}) = \text{selectivity of methanol to styrene+ethylbenzene (mol \%)} = (\text{Sty}_{out} + \text{EB}_{out})/\text{MeOH}_{converted}$$

The term "zeolite" refers to a molecular sieve containing an aluminosilicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

The various embodiments of the present invention can be joined in combination with other inventions of the invention and the listed embodiments herein are not meant to limit the invention. All combinations of various inventions of the invention are enabled, even if not given in a particular example herein.

While illustrative embodiments have been depicted and described, modifications thereof can be made by one skilled in the art without departing from the spirit and scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Also, it is within the scope of this disclosure that the embodiments disclosed herein are usable and combinable with every other embodiment disclosed herein, and consequently, this disclosure is enabling for any and all combinations of the embodiments disclosed herein. Other and further embodiments, versions and examples of the invention may be devised without departing from the basic scope thereof and the scope thereof is determined by the claims that follow.

What is claimed is:

1. A process for making styrene comprising:
providing a $C_1$ source to a reactor comprising a catalyst; and
reacting toluene with the $C_1$ source in the presence of the catalyst to form a product stream comprising ethylbenzene and styrene;

wherein the $C_1$ source is selected from the group consisting of methanol, formaldehyde, formalin, trioxane, methylformcel, paraformaldehyde, methylal, dimethyl ether, and combinations thereof;

wherein the catalyst comprises a nitrogen-substituted zeolite formed through contacting of a zeolite with a nitrogen containing material that subjects the zeolite to the substitution of oxygen with nitrogen within the structure of the zeolite; wherein the zeolite is selected from the group consisting of faujasites;

wherein the nitrogen containing material is selected from the group consisting of ammonia, an alkyl amine, and any combinations thereof;

wherein the catalyst further comprises at least one promoter in an amount ranging from 0.1 wt % to 5 wt % based on the total weight of the catalyst, the promoter selected from the group consisting of Co, Mn, Ti, Zr, V, Nb, K, Cs, Ga, B, P, Rb, Ag, Na, Cu, Mg, Fe, Mo, Ce, and any combinations thereof.

\* \* \* \* \*